United States Patent [19]

Moser

[11] 4,032,657
[45] June 28, 1977

[54] HALOACETANILIDES AS MICROBICIDAL ACTIVE SUBSTANCES

[75] Inventor: Hans Moser, Magden, Switzerland

[73] Assignee: Ciba-Geigy Corporation, Ardsley, N.Y.

[22] Filed: Mar. 27, 1975

[21] Appl. No.: 562,741

[30] Foreign Application Priority Data

Apr. 1, 1974 Switzerland .................. 4510/74
Aug. 23, 1974 Switzerland .................. 11521/74
Aug. 23, 1974 Switzerland .................. 11522/74

[52] U.S. Cl. .......................... 424/309; 260/471 A
[51] Int. Cl.² ................. A01N 9/20; C07C 101/447
[58] Field of Search .............. 260/471 A; 424/309

[56] References Cited

UNITED STATES PATENTS

| 3,712,805 | 1/1973 | Yates et al. ............ 71/111 X |
| 3,763,216 | 10/1973 | Bertrand ............ 260/471 A |
| 3,780,090 | 12/1973 | Akiba et al. ............ 260/471 A |
| 3,780,095 | 12/1973 | Klemm et al. ............ 260/471 A X |
| 3,892,786 | 7/1975 | Baker et al. ............ 260/468 E |

FOREIGN PATENTS OR APPLICATIONS 730,316 1/1973 South Africa

*Primary Examiner*—Richard L. Raymond
*Attorney, Agent, or Firm*—Harry Falber

[57] ABSTRACT

Compounds of the formula

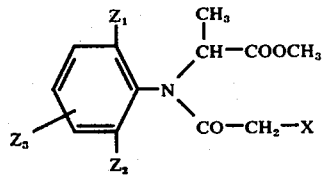

wherein $Z_1$ represents methyl or chlorine, $Z_2$ represents chlorine or bromine, $Z_3$ represents hydrogen or $C_1$–$C_3$ alkyl, and X represents fluorine, chlorine, bromine or iodine, exhibit microbicidal activity, preferably against phytopathogenic fungi.

28 Claims, No Drawings

HALOACETANILIDES AS MICROBICIDAL ACTIVE SUBSTANCES

The present invention relates to compounds of formula I

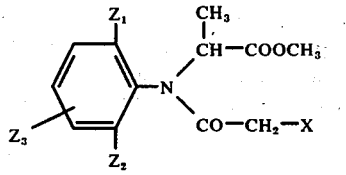

wherein
$Z_1$: represents methyl or chlorine,
$Z_2$: represents chlorine or bromine,
$Z_3$: represents hydrogen or $C_1$–$C_3$-alkyl, and
X: represents fluorine, chlorine, bromine or iodine,
to processes for producing these compounds, as well as to microbicidal compositions containing these new compounds as active substances, and to processes for the control of phytopathogenic fungi and bacteria by application of compounds of formula I.

$C_1$–$C_3$-Alkyl is methyl, ethyl, propyl or isopropyl.

In the German Offenlegungsschrift No. 2,212,268, it is stated in a general manner that N-haloacylated anilinoalkanecarboxylic acid esters have a selective herbicidal action. Only certain N-haloacetylated 2,6-dialkylanilinoacetic acids and their esters are however mentioned and demonstrated as being herbicides. No references are made to a microbicidal, particularly phytofungicidal, action.

In the German Offenlegungsschrift No. 2,311,897, a large number of substituted phenylamines having extraordinarily sharply varying chemical structures are described as herbicides. Likewise in this application, there is no reference made to microbicidal action. The nearest comparable compound, N-chloroacetyl-N-(2,6-dichlorophenyl)-glycine ethyl ester, given in the text is ineffective against phytopathogenic fungi.

The compounds of this invention that are embraced by formula I have not been hitherto described in the literature and are hence new compounds. Remarkably surprising is the fact that they, in contrast to the aforedescribed anilinoacetic acids and anilinoacetic acid esters of the German Offenlegungsschrift No. 2,212,268 and No. 2,311,897, have pronounced phytofungicidal properties. The said compounds have both a preventive and curative action against phytopathogenic fungi in cultivated crops such as, for example, corn, maize, rice, vegetables, sugar beet, soya beans, groundnuts, fruit trees and cultivated plants, particularly, however, grape vines, hops and cucumber plants (cucumbers, punpkins and melons) and solanaceae such as potatoes, tobaco and tomatoes, as well as banana plants, cocoa plants and rubber plants.

It is possible with these active substances to inhibit or destroy fungi occurring on plants or on parts of plants (fruit, blossom, foliage, stems, tubers or roots), whereby also parts of plants subsequently growing remain immune against such fungi. The active substances are effective against phytopathogenic fungi belonging to the following classes: Ascomycetes; Basidiomycetes such as, in particular, rust fungi; *Fungi imperfecti;* but especially against the Oomycetes belonging to the Phycomycetes class, such as Phytophthora, Peronospora, Pseudoperonospora, Pythium or Plasmopara. In addition, the compounds of formula I have a systemic action. They can be used also as seed-dressing agents for protecting seeds (fruit, tubers or grains) and plant cuttings for providing protection against fungus infections, as well as against phytopathogenic fungi present in the soil.

For the broadening or modifying of their sphere of action, the active substances of formula I can be mixed with prior known fungicides, bactericides, fungistatics or bacteriostatics, and also with insecticides, acaricides and herbicides, and, by virtue of their systemic action, which renders possible application to the soil, also with nematicides, molluscicides or rodenticides, with in some cases synergistically enhanced effects being obtained.

A preferred group of compounds of formula I for the control of phytopathogenic fungi is that wherein $Z_1$ represents methyl or chlorine, $Z_2$ represents chlorine, $Z_3$ represents hydrogen or methyl, and X represents chlorine or iodine. These compounds are to be identified as Compound Group Ia.

An important sub-group of compounds of formula I embraces those compounds wherein $Z_1$ represents methyl, $Z_2$ represents chlorine or bromine, $Z_3$ represents hydrogen and X represents chlorine or bromine.

A further important sub-group of compounds of formula I contains compounds wherein $Z_1$ represents methyl, $Z_2$ represents chlorine or bromine, $Z_3$ represents hydrogen and X represents fluorine or iodine.

Another important sub-group of compounds of formula I embraces compounds wherein $Z_1$ and $Z_2$ represent chlorine, $Z_3$ represents hydrogen and X represents fluorine, chlorine, bromine or iodine.

The compounds of formula I possess an asymmetrical carbon atom, and can therefore be split in the usual manner into optical antipodes. The enantiomeric D-form has a stronger microbicidal action compared with that of the L-form. The D-antipodes of compounds of formula I are therefore preferred, and among these compounds those of sub-group Ia.

The compounds of formula I are produced according to the invention by reaction of a compound of formula II

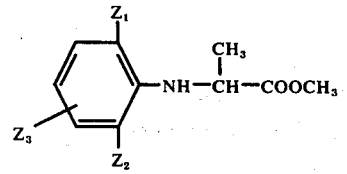

wherein $Z_1$, $Z_2$ and $Z_3$ have the meanings given for formula I, with a haloacetylating agent, preferably with the halide or anhydride of the monofluoro-, monochloro-, monobromo- or monoiodoacetic acid to be used.

The reactions can be performed in the presence or absence of solvents or diluents inert to the reactants. The following are, for example, suitable: aliphatic or aromatic hydrocarbons such as benzene, toluene, xylenes or petroleum ether; halogenated hydrocarbons such as chlorobenzene, methylene chloride, ethylene chloride or chloroform; ethers and ethereal compounds such as dialkyl ether, dioxane or tetrahydrofuran; nitriles such as acetonitrile; N,N-dialkylated amides such as dimethylformamide; also anhydrous acetic acid, ketones such as methyl ethyl ketone, dimethylsulphoxide, and mixtures of such solvents with each other.

Suitable haloacetylating agents to be used are preferably haloacetic acid anhydrides such as, e.g., chloroacetic acid anhydride, and haloacetic acid halides, advantageously haloacetic acid chloride or haloacetic acid bromide. The reaction can however also be performed with the above-mentioned free haloacetic acids, or with their esters or amides.

The reaction temperatures are between 0° and 180° C, preferably between 20° and 100° C. In some cases, especially with the use of haloacetyl halides, haloacetylation is performed in the presence of an acid-binding agent or of a condensation agent. Suitable as such are tertiary amines such as trialkylamines (e.g. triethylamine), pyridine and pyridine bases, or inorganic bases such as the oxides and hydroxides, hydrogen carbonates and carbonates of alkali metals and alkaline-earth metals, as well as sodium acetate. It is possible to use as acid-binding agent also an excess of the aniline derivative of formula II.

The production process according to the invention can be performed also without acid-binding agents; it is then advisable that in some cases nitrogen be passed through to expel the formed hydrogen halide. In other cases, an addition of dimethylformamide as a reaction catalyst is very advantageous.

Details regarding production of the intermediates of formula II can be obtained by reference to the methods described in general for the producton of anilinoalkanoic acid esters in the following publications:

J. Org. Chem. 30, 4101 (1965),
Tetrahedron 1967, 487,
Tetrahedron 1967, 493.

Pure optical antipodes of formula I are produced advantageously by preparing from the aniline of formula III and α-halopropionic acid, e.g. α-bromopropionic acid, the corresponding anilinopropionic acid of formula IV

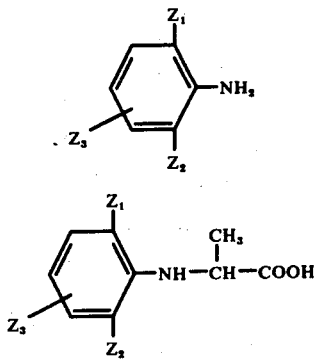

wherein $Z_1$, $Z_2$ and $Z_3$ have the unmodified meaning given for formula I, and reacting this, in a manner known per se, with a nitrogen-containing, optically active base to the corresponding salt. The pure D-form is obtained stepwise by fractional crystallisation of the salt and subsequent liberation of the acid of formula IV enriched with the optical D-antipode, and, optionally, repeat (also several repeats) of salt formation, crystallisation and liberation of the α-anilinopropionic acid of formula IV. From the pure D-form it is then possible to produce in the usual manner, e.g. in the presence of HCl or $H_2SO_4$, with methanol the optical D-configuration of the ester of formula II, which, as stated above, is acylated further to the D-forms of compounds I. Suitable as optically active organic base is, e.g., α-phenylethylamine.

The desired enantiomeric D-form of formula II can however also be obtained from the naturally occurring L-alanine by a process (J. Am. Chem. Soc. 76, 6056) in which the amino group of the alanine is diazotised in the presence of HCl or HBr, and thereby exchanged for halogen, with the simultaneous release of nitrogen to give (L)-α-halopropionic acid, which is afterwards esterified with methanol. There is obtained by reaction with the aniline of formula III, with inversion, predominantly the desired D-form of Compound II, from which there is obtained, by subsequent haloacetylation, the D-form of the final product of formula I.

Except where otherwise stated, the racemic D,L-mixture is meant in the following section in every case where one of the active substances of formula I is mentioned.

The production of active substances of formula I is illustrated by the following Examples 1–3. The temperature values are given in degrees Centigrade.

EXAMPLE 1 a. Production of α-(2-chloro-6-methylanilino)-propionic acid methyl ester (D,L)

35.4 g of 2-chloro-6-methylaniline, 21.3 g of sodium hydrogen carbonate and 84 ml of DL-α-bromopropionic acid methyl ester are stirred for 17 hours at 140° bath temperature. After cooling, the darkly coloured reaction mixture is filtered, and the excess α-bromopropionic acid methyl ester is distilled off in a water-jet vacuum. The residue remaining is fractionally distilled in high vacuum. There is obtained 25.9 g of α-(2-chloro-6-methylanilino)-propionic acid methyl ester, b.p. 72°–75°/0.001 Torr.

b. Production of N-(1'-methoxycarbonyl-ethyl)-N-chloroacetyl-2-chloro-6-methylaniline (D,L)

25.9 g of the ester obtained according to a), 1 ml of dimethylformamide and 200 ml of chlorobenzene are heated to 90° (internal temperature). An addition is made dropwise at this temperature, with stirring, of 10 ml of chloroacetyl chloride. After the evolution of HCl has ceased, stirring is continued for 1 fhour at 120° bath temperature, and the reaction mixture is concentrated in a rotary evaporator. The residue is recrystallised from diisopropyl ether. There is obtained 24.2 g of N-(1'-methoxycarbonylethyl)-N-chloroacetyl-2-chloro-6-methylaniline, m.p. 75°–78°, (Compound No. 1).

EXAMPLE 2 a. Production of α-(2-chloro-6-methylanilino)-propionic acid methyl ester (D,L)

35.4 g of 2-chloro-6-methylaniline, 21.3 g of sodium hydrogen carbonate and 84 ml of DL-α-bromopropionic acid methyl ester are stirred for 17 hours at 140° bath temperature. After cooling, the darkly coloured reaction mixture is filtered, and the excess α-bromopropionic acid methyl ester is distilled off in a water-jet vacuum. The residue remaining is fractionally distilled in high vacuum. There is obtained 25.9 g of α-(2- chloro-6-methylanilino)-propionic acid methyl ester, b.p. 72°–75°/0.001 Torr.

b. Production of N-(1'-methoxycarbonyl-ethyl)-N-fluoroacetyl-2-chloro-6-methylaniline (D,L)

25.9 g of the ester obtained according to a), 1 ml of dimethylformamide and 200 ml of chlorobenzene are heated to 90° (internal temperature). An addition is made dropwise at this temperature, with stirring, of 9.6 ml of fluoroacetyl chloride. After the evolution of HCl has ceased, stirring is maintained for a further 1 hour at 120° bath temperature, and the reaction mixture is then concentrated in a rotary evaporator. The residue is recrystallised from diisopropyl ether. There is obtained 19.5 g of N-(1'-methoxycarbonylethyl)-N-fluoroacetyl-2-chloro-6-methylaniline, m.p. 101°–103°, (Compound No. 5).

EXAMPLE 3 a. Production of α-(2,6-dichloroanilino)-propionic acid methyl ester (D,L)

40.5 g of 2,6-dichloroaniline, 21 g of sodium hydrogen carbonate and 84 ml of DL-α-bromopropionic acid methyl ester are stirred in a sulphonating flask for 2 days at 140° bath temperature. After cooling, the reaction mixture is poured into water and extracted with ethyl acetate. The combined ethyl acetate fractions are extracted once with saturated sodium chloride solution, dried over sodium sulphate and concentrated in a rotary evaporator. The excess α-bromopropionic acid methyl ester is recovered in a water-jet vacuum. The darkly coloured residue remaining is fractionally distilled in high vacuum. There is obtained 23.6 g of α-(2,6-dichloroanilino)-propionic acid methyl ester; b.p. 85°–87°/0.001 Torr.

b. Production of N-(1'-methoxycarbonyl-ethyl)-N-chloroacetyl-2,6-dichloroaniline (D,L)

18.4 g of α-(2,6-dichloroanilino)-propionic acid methyl ester, 1 ml of dimethylformamide and 100 ml of chlorobenzene are heated to 100° (internal temperature). An addition is made dropwise at this temperature, with stirring, of 8 ml of chloroacetyl chloride. After the evolution of HCl has ceased, stirring is maintained for 1 hour at 130°–140° bath temperature. The reaction mixture is allowed to cool to room temperature, the solvent is removed in a rotary evaporator, and the yellow oil remaining as residue is crystallised from diisopropyl ether. There is obtained 16 g of final product having a melting point of 82°–85° (Compound No. 10).

There are produced in this manner or in a similar manner the following (D,L) compounds: ($Z_1$ = 2-position)

| Comp. No. | $Z_1$ | $Z_2$ | $Z_3$ | X | Physical constants |
|---|---|---|---|---|---|
| 1 | $CH_3$ | Cl | H | Cl | m.p. 75 – 78° |
| 2 | $CH_3$ | Br | H | Cl | |
| 3 | $CH_3$ | Cl | H | Br | m.p. 70 – 72° |
| 4 | $CH_3$ | Br | H | Br | |
| 5 | $CH_3$ | Cl | H | F | m.p. 101 – 103° |
| 6 | $CH_3$ | Br | H | F | |
| 7 | $CH_3$ | Cl | H | J | m.p. 75 – 78° |
| 8 | $CH_3$ | Br | H | J | |
| 9 | Cl | Cl | H | F | m.p. 139 – 142° |
| 10 | Cl | Cl | H | Cl | m.p. 82 – 85° |
| 11 | Cl | Cl | H | Br | m.p. 68 – 70° |

-continued

| Comp. No. | $Z_1$ | $Z_2$ | $Z_3$ | X | Physical constants |
|---|---|---|---|---|---|
| 12 | Cl | Cl | H | J | m.p. 57 – 59° |
| 13 | $CH_3$ | Cl | 3-$CH_3$ | Cl | |
| 14 | $CH_3$ | Cl | 5-$CH_3$ | Cl | |
| 15 | Cl | Cl | 3-$CH_3$ | Cl | |
| 16 | $CH_3$ | Cl | 4-$CH_3$ | Cl | |
| 17 | Cl | Cl | 4-$C_2H_5$ | Cl | |
| 18 | Cl | Cl | 4-iso$C_3H_7$ | Cl | |
| 19 | $CH_3$ | Cl | 3-$CH_3$ | Br | |
| 20 | $CH_3$ | Cl | 3-$CH_3$ | J | |
| 21 | Cl | Cl | 3-$CH_3$ | Br | |
| 22 | Cl | Cl | 3-$CH_3$ | J | |
| 23 | $CH_3$ | Cl | 5-$CH_3$ | Br | |
| 24 | $CH_3$ | Cl | 5-$CH_3$ | J | |

In the following there are characterised D-configurations of the above-mentioned compounds as well as of their intermediates:

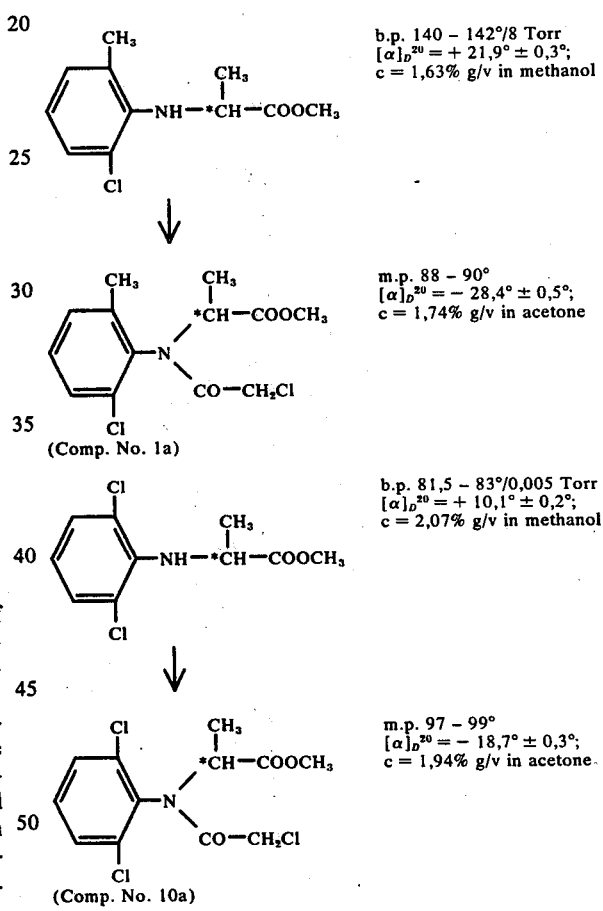

For the broadening of their sphere of action, the compounds of formula I can be used together with other suitable pesticides or suitable active substances promoting plant growth.

The compounds of formula I can be used on their own or together with suitable carriers and/or other additives. Suitable carriers and additives can be solid or liquid, and they correspond to the substances common in formulation practice, such as, e.g., natural or regenerated mineral substances, solvents, dispersing agents, wetting agents, adhesives, thickeners, bonding agents or fertilisers.

The content of active substance in commercial compositions is between 0.1 and 90%.

For application, the compounds of formula I can be in the following forms (the percentage of weight figures in brackets represent advantageous amounts of active substance):

solid preparations:
dusts and scattering agents (up to 10%); granulates, coated granulates, impregnated granulates and homogeneous granulates (1 to 80%);

liquid preparations:
a. water-dispersible active-substance concentrates: wettable powders and pastes (25 –90% in the commercially packed form, 0.01 to 15% in the ready-for-use solution);
emulsion concentrates and solution concentrates (10 to 50%; 0.01 to 15% in the ready-for-use solution);
b. solutions (0.1 to 20%).

The active substances of formula I of the present invention can be formulated, for example, as follows:

Dusts:
The following substances are used to produce a) a 5% dust and b) a 2% dust:
a. 5 parts of active substance, 95 parts of talcum;
b. 2 parts of active substance, 1 part of highly dispersed silicic acid, 97 parts of talcum.
The active substances are mixed with the carriers and can be applied as a dust in this form.

Granulate:
The following substances are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3 – 0.8 mm).

The active substance is mixed with epichlorohydrin and the mixture is dissolved in 6 parts of acetone; there are then added polyethylene glycol and cetyl polyglycol ether. The solution obtained is sprayed onto kaolin, and the acetone is subsequently evaporated off in vacuo. A microgranulate of this kind is advantageously used for the control of soil fungi.

Wettable powders:
The following constituents are used to produce a) a 70%, b) a 40%, c) and d) a 25%, and e) a 10% wettable powder:
a. 70 parts of active substance,
5 parts of sodium dibutyl-naphthyl sulphonate,
3 parts of naphthalenesulphonic acid/phenolsulphonic acid/formaldehyde condensate 3:2:1,
10 parts of kaolin,
12 parts of Champagne chalk;
b. 40 parts of active substance,
5 parts of sodium lignin sulphonate,
1 part of sodium dibutyl-napthalene sulphonate,
54 parts of silicic acid;
c. 25 parts of active substance,
4.5 parts of calcium lignin sulphonate,
1.9 parts of Champagne chalk/hydroxy ethyl cellulose mixture (1:1),
1.5 parts of sodium dibutyl naphthalene sulphonate,
19.5 parts of silicic acid,
19.5 parts of Champagne chalk,
28.1 parts of kaolin;
d. 25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;
e. 10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed with the additives in suitable mixers, and the mixture is ground on the appropriate mills and rollers. There are obtained wettable powders which have excellent wetting and suspension properties, and which can be diluted with water to give suspensions of any desired concentration, which suspensions can be used, in particular, for leaf application.

Emulsifiable concentrate:
The following substances are used to produce a 25% emulsifiable concentrate:
25 parts of active substance,
2.5 parts of epoxidised vegetable oil,
10 parts of an alkylarylsulphonate/fatty alcohol-polyglycol ether mixture,
5 parts of dimethylformamide,
57.5 parts of xylene.

It is possible to produce from such concentrates, by dilution with water, emulsions of any desired concentration, which are particularly suitable for leaf application.

EXAMPLE 4

Action against Phytophthora infestans on Solanum lycopersicum (= tomatoes)

I*a*. Residual preventive action

After 3 weeks' cultivation, Solanum lycopersicum plants are the variety "Roter Gnom" (red gnome) are infested, after being sprayed with a liquor containing 0.05% of active substance (prepared with the active substance formulated as a wettable powder) and dried, with a zoospore suspension of *Phytophthora infestans*. The plants ten remain for 6 days in a controlled-atmosphere chamber at 18° to 20° with high atmospheric humidity produced by an artificial spray. Typical leaf spots appear after this period of time. Their number and size serve as the evaluation criterion for the tested substance.

I*b*. Curative action

After 3 weeks' cutivation, tomato plants of the variety Roter Gnom are sprayed with a zoospore suspension of the fungus, and incubated in a chamber at 18° to 20° with saturated atmospheric humidity. The treatment is interrupted after 24 hours. After drying of the plants, they are sprayed with a liquor containing the active substance, made up as a wettable powder, at a concentration of 0.05%. After drying of the sprayed-on coating, the plants are allowed to stand in the moist-atmosphere chamber for 4 days. The number and size of the typical leaf spots are taken as a criterion for assessing the effectiveness of the substances tested.

II Preventive systemic action

The active substance formulated as a wettable powder is applied at a concentration of 0.05% (relative to the volume of soil) to the surface of the soil of 3-week-old potted tomato plants of the variety Roter Gnom. After a waiting time of 3 days, the underside of the leaves of the plants is sprayed with a zoospore suspension of Phytophthora infestans. The plants are then stored for 5 days in a spray chamber at 18° to 20° with a saturated atmosphere. Typical leaf spots form after this length of time; their number and size are taken as a basis for the assessment of the effectiveness of the substances tested.

| Table to Example 4 (average values) | | | |
|---|---|---|---|
| Comp. No. | Fungus infestation in % | Comp. No. | Fungus infestation in % |
| 1 | 0–5 % | 10 | 0–5 % |
| 1a | 0–5 % | 10a | 0–5 % |
| 2 | <20 % | 12 | <20 % |
| 3 | 20–40 % | 13 | 0–5 % |
| 4 | 20–40 % | 14 | 0–5 % |
| 5 | <20 % | 15 | 0–5 % |
| 6 | 20–40 % | 16 | <20 % |
| 7 | <20 % | 18 | <20 % |
| 8 | <20 % | 20 | <20 % |
| 9 | 0–5 % | 22 | <20 % |

In identical tests, compounds Nos. 1, 10, 13, 14 and 15 reduced with an applied concentration of only 0.02% fungus infestation to <20%; compounds Nos. 1a and 10a (D-configurations) to 0 – 5%.

EXAMPLE 5

Action against *Plasmopara viticola* (Bert. et Curt.) (Berl. et DeToni) on grapevines a. Residual preventive action Grapevine cuttings of the variety "Chasselas" are grown in a greenhouse. Three plants in the 10-leaf stage are sprayed with a liquor prepared from the active substance formulated as a wettable powder (0.05% of active substance). After drying of the applied coating, the plants are uniformly infested on the underside of the leaves with the spore suspension of the fungus. The plants are subsequently held for 8 days in a moist chamber. Clear symptoms of disease appear after this time on the control plants. Number and size of the infection sites on the treated plants provide a criterion for evaluation of effectiveness of the substances tested.

b. Curative action

Grapevine cuttings of the variety Chasselas are cultivated in a greenhouse, and infested in the 10-leaf stage by application of a spore suspension of Plasmopara viticola to the underside of the leaves. After standing for 24 hours in a moist chamber, the plants are sprayed with a liquor containing 0.05% of active substance, which has been prepared from a wettable powder of the active substance. The plants are subsequently kept for a further 7 days in the moist chamber. Disease symptoms appear on the control plants after this period of time, and the number and size of the infection sites on the treated plants serve as an evaluation criterion for the effectiveness of the substances tested.

The compounds of formula I exhibit in these two tests a predominantly good leaf-fungicidal action. Fungus infestation is almost completely eliminated (0–5% infestation) with Compounds Nos. 1, 1a, 9, 10, 10a, 13, 14 and 15.

EXAMPLE 6

Action against *Pythium debaryanum* on Beta vulgaris (sugar beet)

a. Action after application to soil

The fungus is cultivated on sterile oat grains, and added to a soil/sand mixture. The soil infested in this way is placed into flower pots and sown with sugar-beet seeds. Immediately after sowing, the test preparations, formulated as wettable powders are poured as aqueous suspensions over the soil (20 ppm of active substance, relative to the volume of soil). The pots are afterwards left to stand for 2–3 weeks in a greenhouse at 20°–24° C. The soil is maintained throughout uniformly moist by a light spraying with water. In the evaluation of the tests, the germination of the sugar beet plants and the proportion of healthy plants and diseased plants are determined.

b. Action after dressing application

The fungus is cultivated on sterile oat grains, and added to a soil/sand mixture. The soil infested in this way is placed into flower pots and sown with sugar-beet seeds that have been dressed with the test preparations formulated as dressing powders (1000 ppm of active substance relative to the weight of seed). The sown pots are allowed to stand for 2–3 weeks in a greenhouse at 20°–24° C. The soil is maintained uniformly moist by a light spraying with water. In the evaluation of the tests, the germination of the sugar-beet plants and the proportion of healthy plants and diseased plants are determined.

After treatment with the active substances of formula I, both under test conditions a) and test conditions b), more than 80% of the sugar-beet plants sprouted and had a good appearance. With application of Compounds Nos. 7, 8, 12, 20 and 22, there was an increase in the proportion of healthily germinated plants to 90% and over. In the case of the untreated control plants, less than 20% of the plants germinated and these had in general a diseased appearance.

I claim:

1. A compound of formula I wherein
$Z_1$ represents methyl or chlorine,
$Z_2$ represents chlorine or bromine,
$Z_3$ represents hydrogen or $C_1$–$C_3$-alkyl, and
X represents fluorine, chlorine, bromine or iodine.

2. The compound according to claim 1, wherein
$Z_1$ represents methyl or chlorine,
$Z_2$ represents chlorine,
$Z_3$ represents hydrogen or methyl, and
X represents chlorine or iodine.

3. The compound according to claim 1, wherein
$Z_1$ represents methyl,
$Z_2$ represents chlorine or bromine,
$Z_3$ represents hydrogen, and
X represents chlorine or bromine.

4. The compound according to claim 1, wherein
$Z_1$ represents methyl,
$Z_2$ represents chlorine or bromine,
$Z_3$ represents hydrogen, and
X represents fluorine or iodine.

5. The compound according to claim 1, wherein
$Z_1$ and $Z_2$ represent chlorine,
$Z_3$ represents hydrogen, and
X represents fluorine, chlorine, bromine or iodine.

6. The compound N-(1'-methoxycarbonyl-ethyl)-N-chloroacetyl-2-methyl-6-chloroaniline according to claim 1.

7. The compound N-(1'-methoxycarbonyl-ethyl)-N-chloroacetyl-2, 6-dichloroaniline according to claim 1.

8. The compound N-(1'-methoxycarbonyl-ethyl)-N-iodoacetyl-2, 6-dichloroaniline according to claim 1.

9. The compound N-(1'-methoxycarbonyl-ethyl)-N-iodoacetyl-2-methyl-6-chloroaniline according to claim 1.

10. The compound N-(1'-methoxycarbonyl-ethyl)-N-chloroacetyl-2, 3-dimethyl-6-chloroaniline according to claim 1.

11. The compound N-(1'-methoxycarbonyl-ethyl)-N-chloroacetyl-2, 5-dimethyl-6-chloroaniline according to claim 1.

12. The compound N-(1'-methoxycarbonyl-ethyl)-N-chloroacetyl-2, 6-dichloro-3methylaniline according to claim 1.

13. The compound N-(1'-methoxycarbonyl-ethyl)-N-fluoroacetyl-2-methyl-6-chloroaniline according to claim 1.

14. The compound N-(1'-methoxycarbonyl-ethyl)-N-fluoroacetyl-2, 6-dichloroaniline according to claim 1.

15. The enantiomeric D-configuration of compounds of formula I according to claim 1.

16. A fungicidal composition containing as active substance a fungicidally effective amount of a compound of formula I

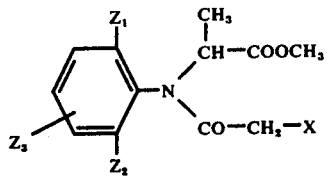

wherein
$Z_1$ represents methyl or chlorine,
$Z_2$ represents chlorine or bromine,
$Z_3$ represents hydrogen or $C_1$–$C_3$-alkyl, and
X represents fluorine, chlorine, bromine or iodine, together with a suitable carrier therefor.

17. Composition according to claim 16 containing an active substance of formula I, wherein
$Z_1$ represents methyl or chlorine,
$Z_2$ represents chlorine,
$Z_3$ represents hydrogen or methyl, and
X represents chlorine or iodine.

18. Composition according to claim 16 containing an active substance of formula I, wherein
$Z_1$ represents methyl,
$Z_2$ represents chlorine or bromine,
$Z_3$ represents hydrogen, and
X represents chlorine or bromine.

19. Composition according to claim 16 containing an active substance of formula I, wherein
$Z_1$ represents methyl,
$Z_2$ represents chlorine or bromine,
$Z_3$ represents hydrogen, and
X represents fluorine or iodine.

20. Composition according to claim 16 containing an active substance of formula I, wherein
$Z_1$ and $Z_2$ represent chlorine,
$Z_3$ represents hydrogen, and
X represents fluorine, chlorine, bromine or iodine.

21. Composition according to claim 16 containing the active substance N-(1'-methoxycarbonyl-ethyl)-N-chloroacetyl-2-methyl-6-chloroaniline.

22. Composition according to claim 16 containing the active substance N-(1'-methoxycarbonyl-ethyl)-N-chloroacetyl-2, 6-dichloroaniline.

23. Composition according to claim 16 containing the active substance N-(1'-methoxycarbonyl-ethyl)-N-iodoacetyl-2, 6-dichloroaniline.

24. Composition according to claim 16 containing the active substance N-(1'-methoxcarbonyl-ethyl)-N-iodoacetyl-2-methyl-6-chloroaniline.

25. Composition according to claim 16 containing the active substance N-(1'methoxycarbonyl-ethyl)-N-chloroacetyl-2, 3-dimethyl-6-chloroaniline.

26. Composition according to claim 16 containing the active substance N-(1'-methoxycarbonyl-ethyl)-N-chloroacetyl-2, 5-dimethyl-6-chloroaniline.

27. Composition according to claim 16 containing the active substance N-(1'-methoxycarbonyl-ethyl)-N-chloroacetyl-2, 6-dichloro-3-methylaniline.

28. A method for the control of phytopathogenic fungi which comprises applying to the locus thereof a fungicidally effective amount of a compound of formula I according to claim 16.

* * * * *